(12) United States Patent
Bronson et al.

(10) Patent No.: US 8,715,331 B2
(45) Date of Patent: May 6, 2014

(54) STENT EDGE PROTECTION AND METHODS

(75) Inventors: Mary Bronson, Elk River, MN (US); Gerald Grabowski, Plymouth, MN (US); Andrzej Malewicz, Minneapolis, MN (US); Kathy Prindle, Robbinsdale, MN (US); Zachary J. Tegels, Minneapolis, MN (US); Karen Turner, Lino Lakes, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 572 days.

(21) Appl. No.: 12/187,148

(22) Filed: Aug. 6, 2008

(65) Prior Publication Data

US 2010/0036477 A1  Feb. 11, 2010

(51) Int. Cl.
*A61F 2/06* (2013.01)
*A61F 2/954* (2013.01)
*A61F 2/958* (2013.01)
*A61M 25/10* (2013.01)

(52) U.S. Cl.
CPC ............. *A61F 2/954* (2013.01); *A61F 2/958* (2013.01)
USPC ........................................ 623/1.11; 606/194

(58) Field of Classification Search
CPC ............................. A61F 2/954; A61F 2/958
USPC ........ 606/194; 623/1.11; 604/101.01, 101.04, 604/284
See application file for complete search history.

(56) References Cited

U.S. PATENT DOCUMENTS

| | | | |
|---|---|---|---|
| 4,950,227 A | 8/1990 | Savin et al. | |
| 5,108,416 A | 4/1992 | Ryan et al. | |
| 5,769,819 A | 6/1998 | Schwab et al. | |
| 5,836,965 A | 11/1998 | Jendersee et al. | |
| 5,843,027 A * | 12/1998 | Stone et al. | 606/194 |
| 5,902,331 A * | 5/1999 | Bonner et al. | 606/129 |
| 5,935,135 A | 8/1999 | Bramfitt et al. | |
| 6,210,429 B1 | 4/2001 | Vardi et al. | |
| 6,280,412 B1 | 8/2001 | Pederson, Jr. et al. | |
| 6,325,826 B1 | 12/2001 | Vardi et al. | |
| 6,432,080 B2 | 8/2002 | Pederson, Jr. et al. | |
| 6,432,129 B2 | 8/2002 | DiCaprio | |
| 6,517,548 B2 | 2/2003 | Lorentzen Cornelius et al. | |
| 6,533,755 B2 | 3/2003 | Adams | |
| 6,764,504 B2 | 7/2004 | Wang et al. | |
| 6,948,223 B2 | 9/2005 | Shortt | |
| 7,220,275 B2 | 5/2007 | Davidson et al. | |

(Continued)

FOREIGN PATENT DOCUMENTS

| | | |
|---|---|---|
| EP | 0457456 | 11/1991 |
| EP | 0875263 | 2/2004 |

(Continued)

*Primary Examiner* — Kathleen Holwerda
*Assistant Examiner* — Sarah W Aleman
(74) *Attorney, Agent, or Firm* — Seager, Tufte & Wickhem LLC

(57) ABSTRACT

A catheter assembly and related methods directed to stent edge protection for an edge of a stent. One example stent edge protect member is positioned with a distal end portion of the stent edge protect member arranged proximal of and adjacent to a proximal end of the stent. The stent edge protect member defines an outer surface that transitions from an outer surface of the stent at the proximal end of the stent to an outer surface of the catheter branch on which the stent edge protect member is positioned. The stent edge protect member can be positioned on a single catheter branch or multiple catheter branches.

15 Claims, 9 Drawing Sheets

(56) References Cited

U.S. PATENT DOCUMENTS

| | | |
|---|---|---|
| 2001/0011179 A1 | 8/2001 | Adams |
| 2002/0065475 A1 | 5/2002 | Meguro et al. |
| 2003/0074044 A1* | 4/2003 | Randby et al. ............... 623/1.11 |
| 2003/0139803 A1* | 7/2003 | Sequin et al. ................ 623/1.16 |
| 2003/0181923 A1 | 9/2003 | Vardi et al. |
| 2004/0148000 A1* | 7/2004 | Bilge ........................ 623/1.11 |
| 2005/0027344 A1* | 2/2005 | Eidenschink ................ 623/1.11 |
| 2005/0060027 A1* | 3/2005 | Khenansho et al. ......... 623/1.35 |
| 2005/0149161 A1 | 7/2005 | Eidenschink et al. |
| 2005/0192656 A1* | 9/2005 | Eidenschink ................ 623/1.11 |
| 2005/0203563 A9 | 9/2005 | Pederson, Jr. et al. |
| 2006/0009832 A1 | 1/2006 | Fisher |
| 2008/0027528 A1 | 1/2008 | Jagger et al. |
| 2008/0051705 A1* | 2/2008 | Von Oepen et al. ......... 623/1.11 |

FOREIGN PATENT DOCUMENTS

| | | |
|---|---|---|
| WO | 2004/035127 | 4/2004 |
| WO | 2005/004971 | 1/2005 |
| WO | 2006/002268 | 1/2006 |
| WO | 2006/068926 | 6/2006 |

* cited by examiner

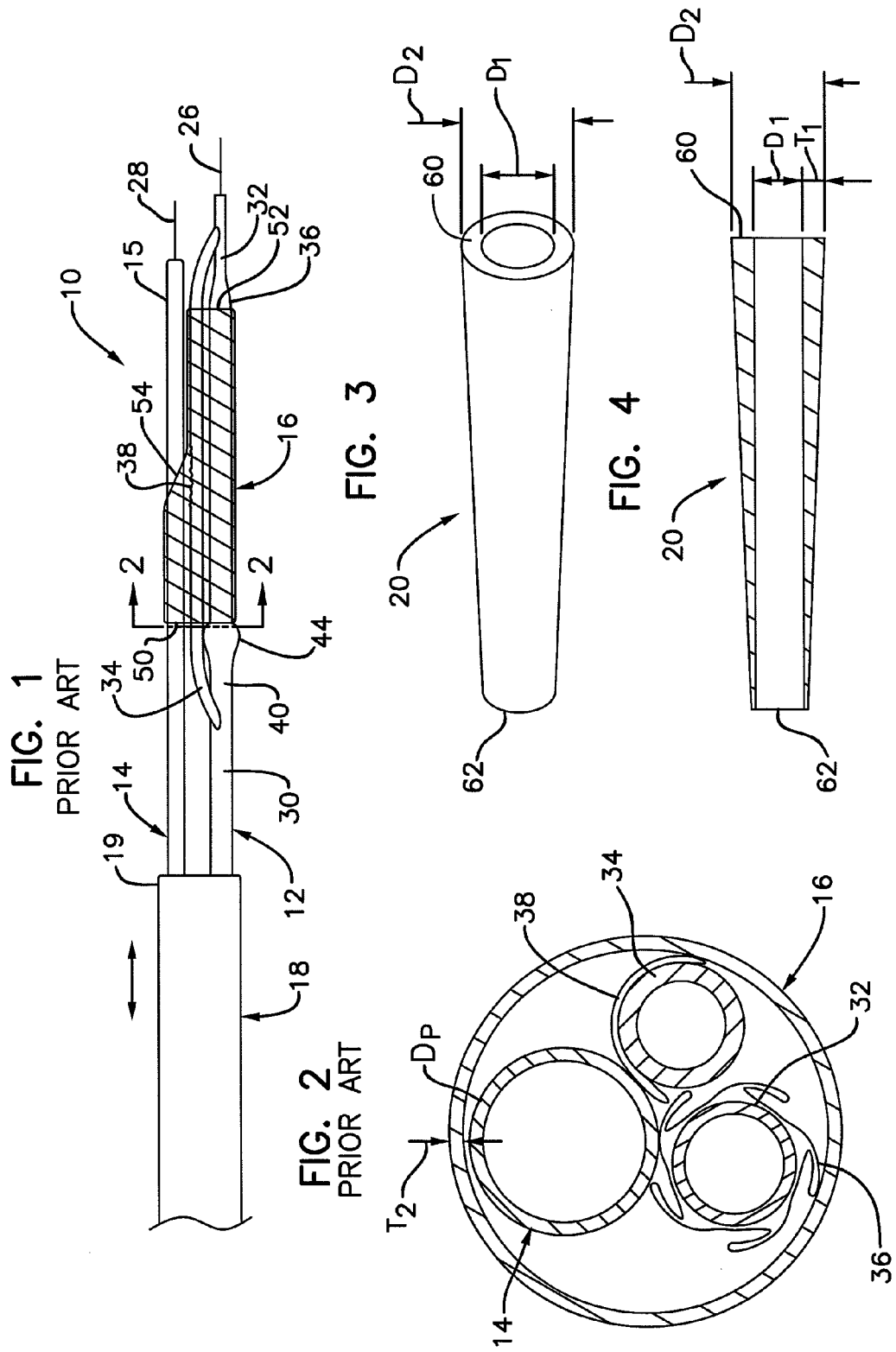

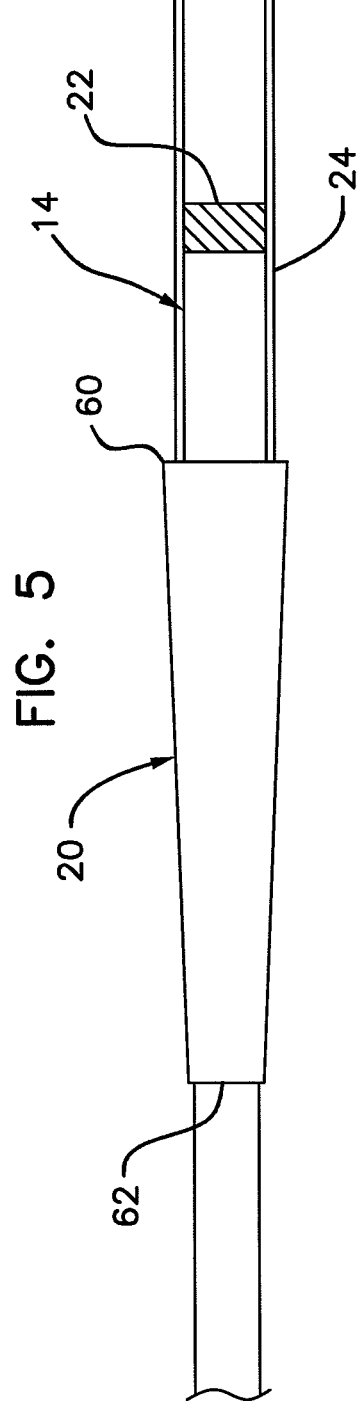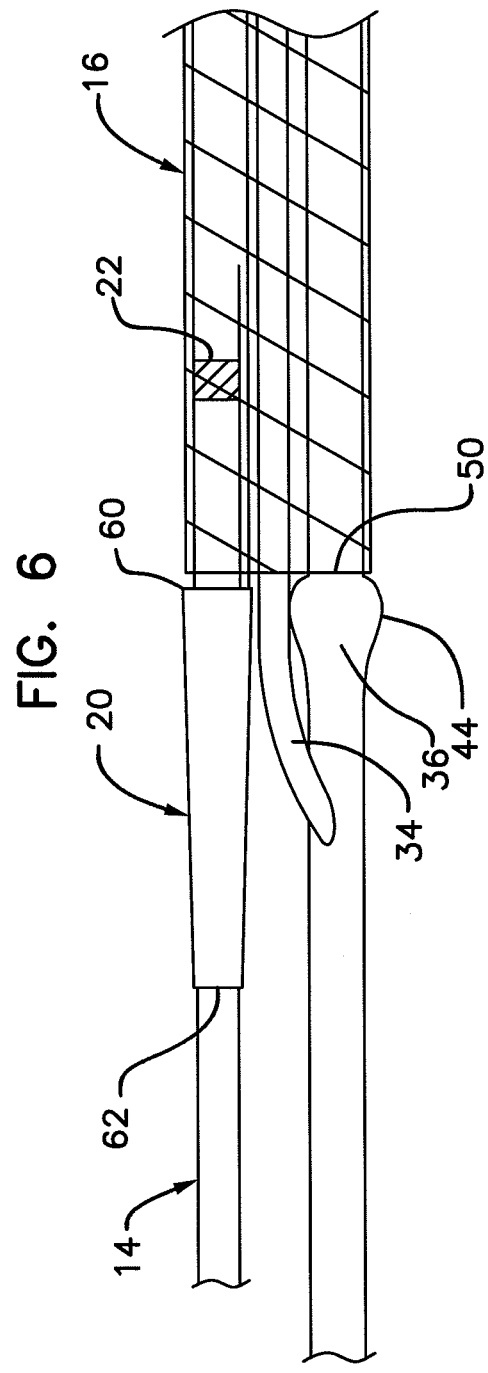

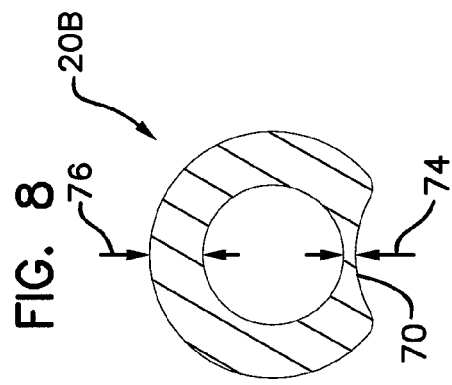
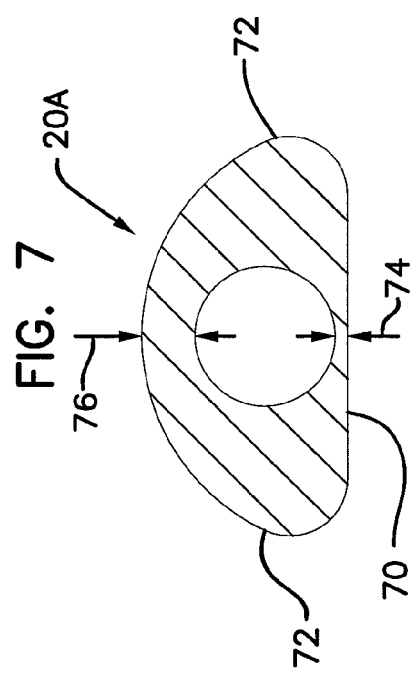
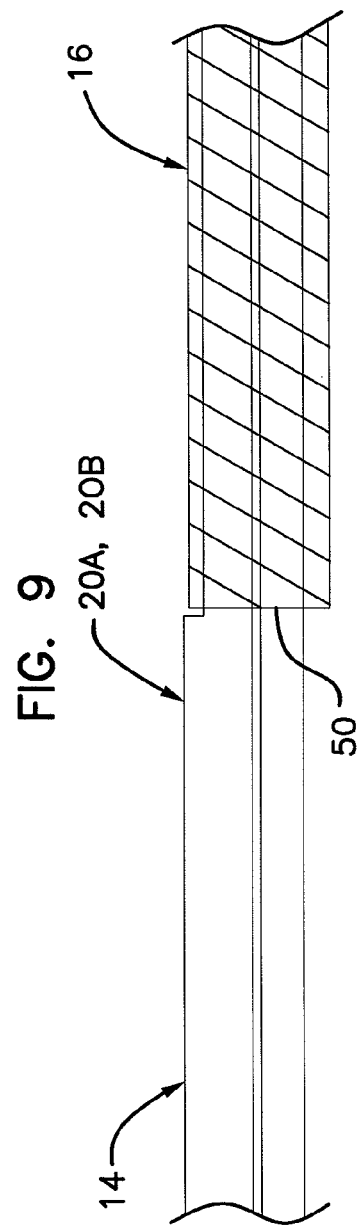

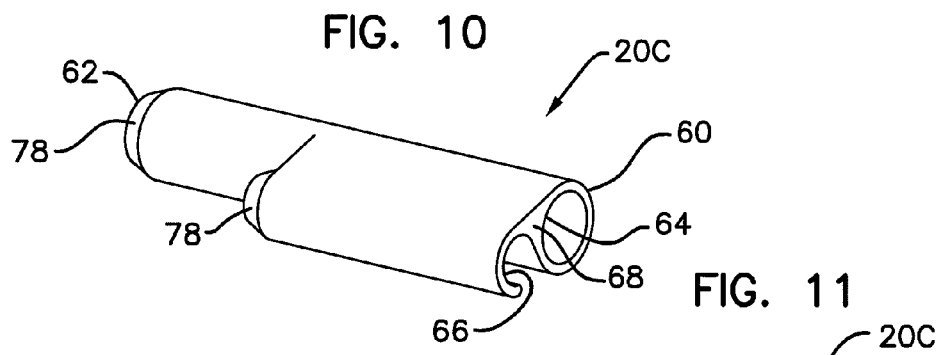
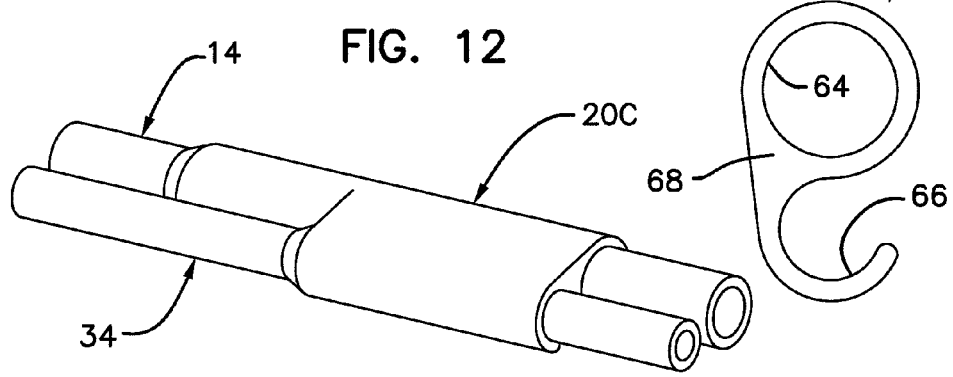
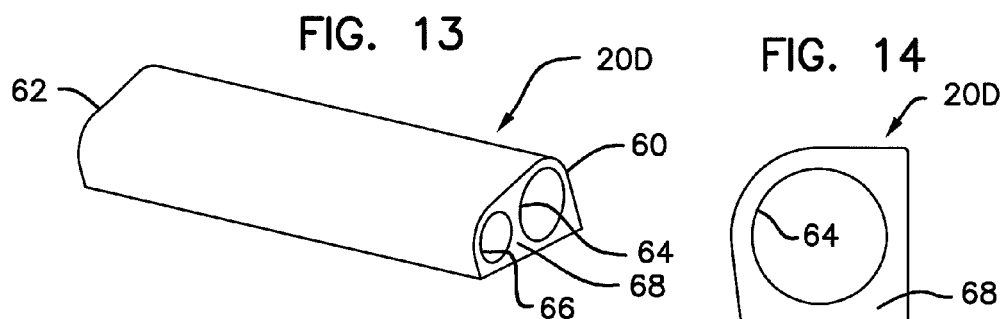
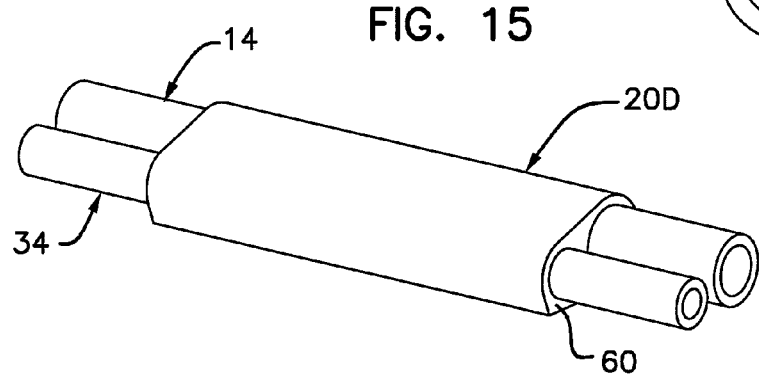

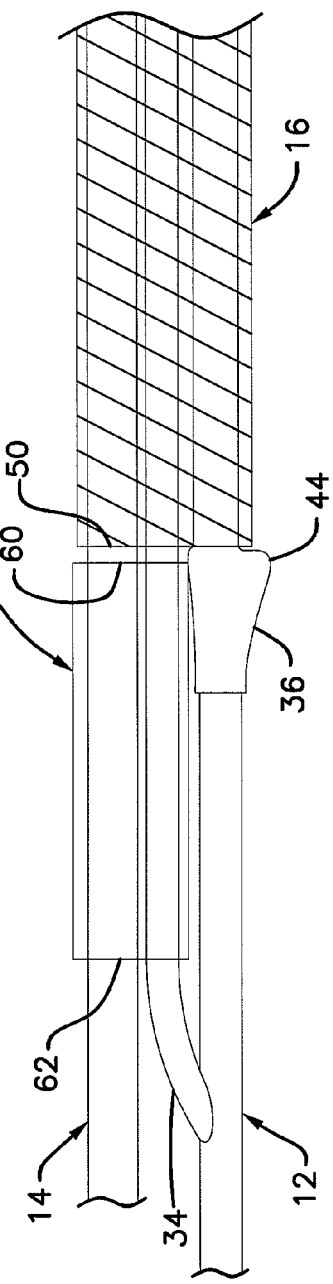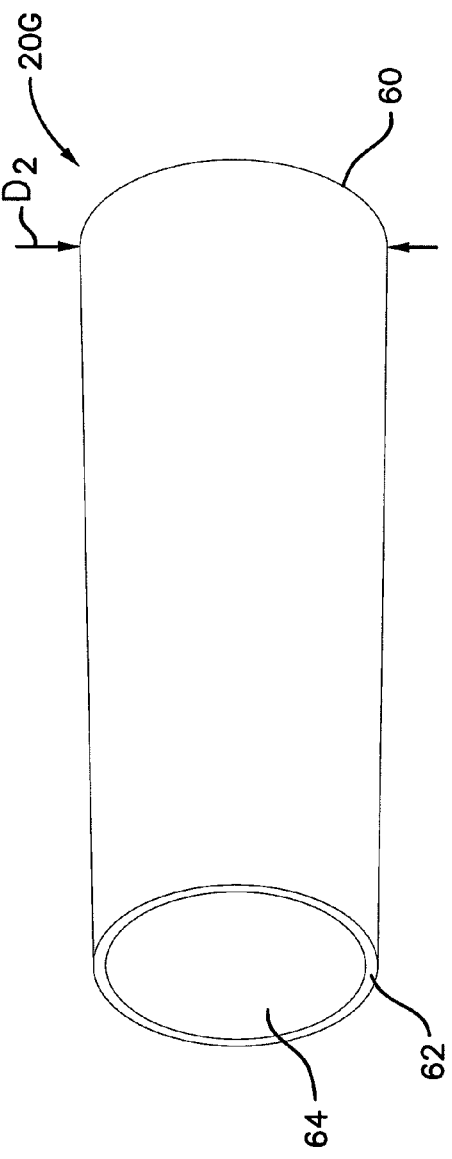

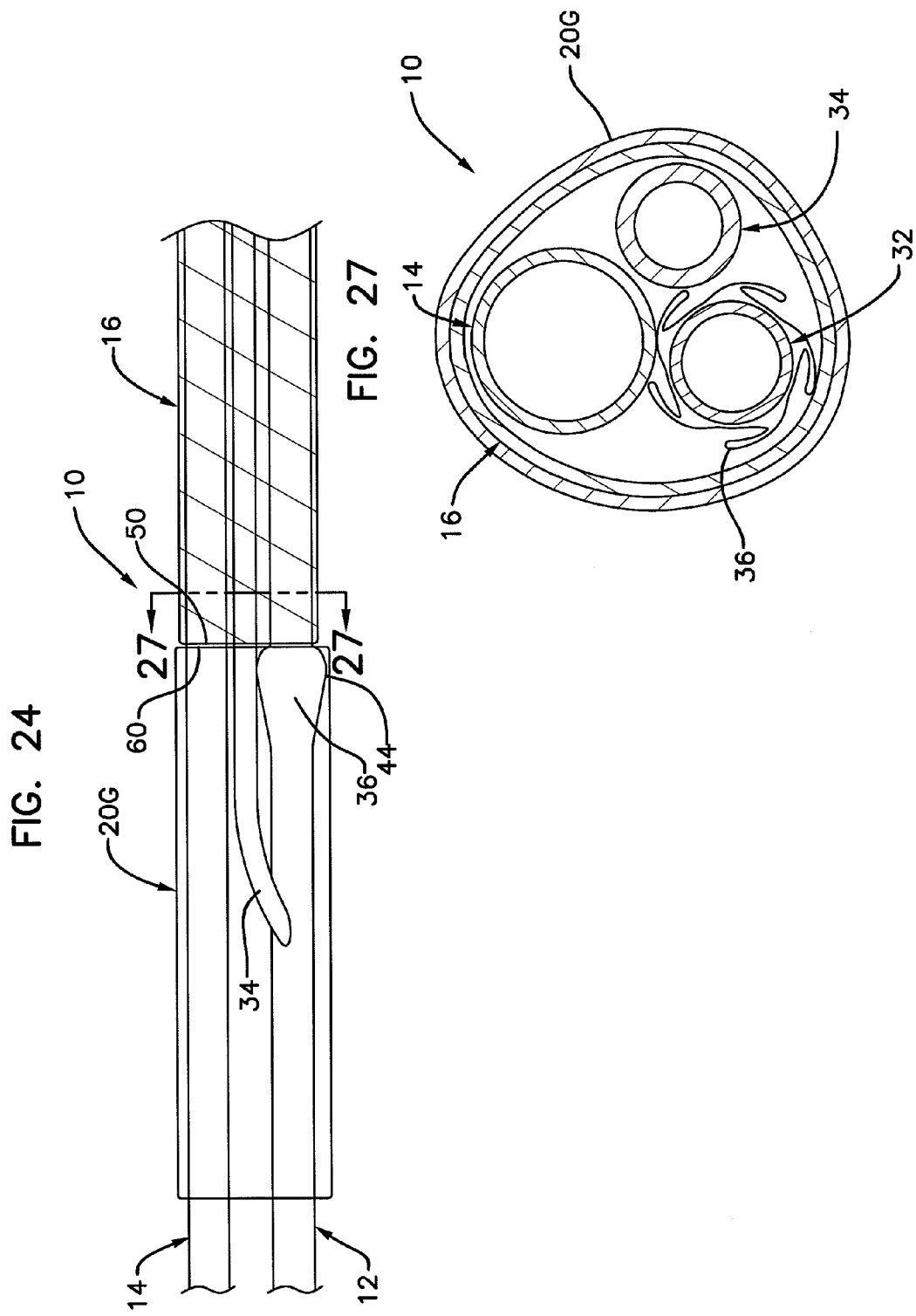

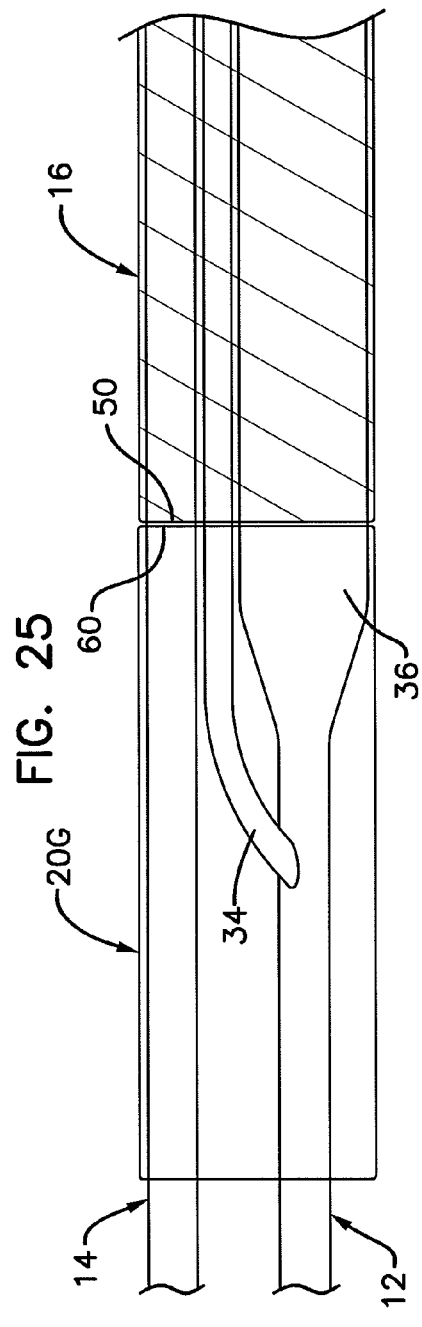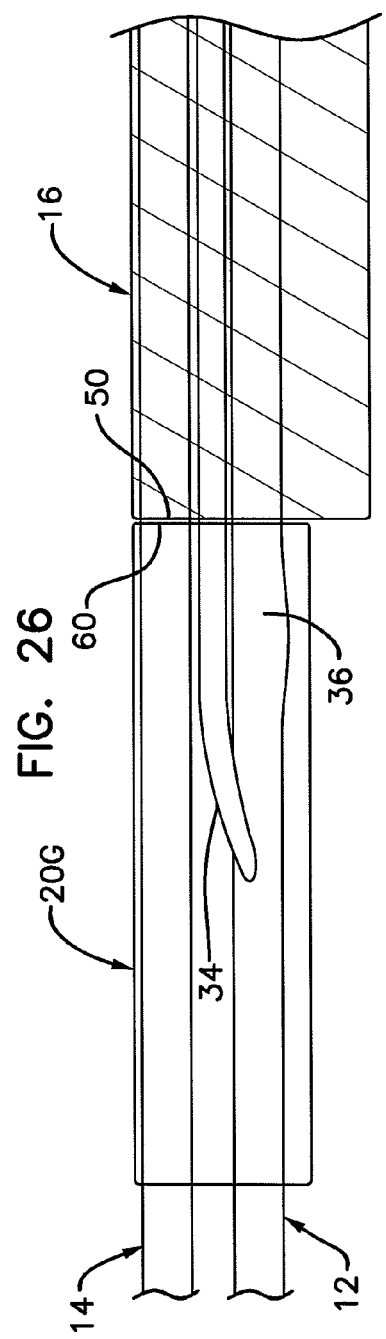

STENT EDGE PROTECTION AND METHODS

TECHNICAL FIELD

This disclosure relates to catheter assemblies configured for treatment of a vessel bifurcation. Preferred arrangements provide for protection of edges of a stent during delivery of the stent at a vessel bifurcation treatment site.

BACKGROUND

Catheters are used with stents and inflatable structures to treat conditions such as strictures, stenoses, and narrowing in various parts of the body. Various catheter designs have been developed for the dilatation of stenoses and to deliver and deploy stents at treatment sites within the body.

Stents are typically intraluminally placed by a catheter within a vein, artery, or other tubular shaped body organ for treating conditions such as, for example, occlusions, stenoses, aneurysms, dissections, or weakened, diseased, or abnormally dilated vessels or vessel walls, by expanding the vessels or by reinforcing the vessel walls. Once delivered, the stents can be expanded using one or more inflatable members such as balloons. Stents can improve angioplasty results by preventing elastic recoil and remodeling of the vessel wall and treating dissections in blood vessel walls caused by balloon angioplasty of coronary arteries. Stents can also be used as a drug delivery medium for treatment of damaged portions of a vessel.

While conventional stent technology is relatively well developed, stent technologies related to treatment of the region of a vessel bifurcation are still being developed. One challenge related to treatment of a vessel bifurcation involves protecting edges of the stent during delivery and repositioning of the stent to a vessel bifurcation treatment site.

SUMMARY OF THE DISCLOSURE

The present disclosure relates to catheter assemblies having first and second catheter branches or shafts that are configured for advancement over separate guidewires to a treatment site within a patient. Some catheter assemblies are used to deliver a stent to a vessel bifurcation treatment site within a patient. A portion of the stent extends over both of the catheter branches. At least one of the catheter branches includes proximal edge protection features that provide protection of a proximal edge or proximal end portion of the stent. The proximal edge protection features can provide proximal edge protection for only portions around a periphery (e.g. circumference) of the stent proximal edge. Alternatively, the proximal edge protection features can be configured to provide proximal edge protection around substantially all of the stent proximal edge. The proximal edge protection features can be integral with one or more of the catheter branches. The proximal edge protection features can also be provided as separate pieces that are positioned on one or more of the catheter branches and held in place using, for example, adhesives or heat bonding.

There is no requirement that an arrangement include all features characterized herein to obtain some advantage according to this disclosure.

BRIEF DESCRIPTION OF THE DRAWINGS

FIG. 1 is a schematic side view of a stent delivery system constructed according to principles of this disclosure.

FIG. 2 is a schematic cross-sectional view of the stent delivery system of FIG. 1.

FIG. 3 is a schematic perspective view of a single catheter branch edge protect member in accordance with principles of the present disclosure.

FIG. 4 is a schematic cross-sectional side view of the edge protect member shown in FIG. 3.

FIG. 5 is a schematic side view of the edge protect member shown in FIG. 3 positioned on a catheter branch.

FIG. 6 is a schematic partial side view of the stent delivery system shown in FIG. 1 and further including the edge protect member shown in FIG. 3.

FIG. 7 is a schematic cross-sectional view of another example edge protect member in accordance with principles of the present disclosure.

FIG. 8 is a schematic cross-sectional view of yet another example edge protect member in accordance with principles of the present disclosure.

FIG. 9 is a schematic side view of a portion of the stent delivery system shown in FIG. 1 and further including one of the proximal edge protect members shown in FIGS. 7 and 8.

FIG. 10 is a schematic perspective view of another example edge protect member in accordance with the present disclosure, the edge protect member configured to extend around a circumference of one catheter branch and releasable mount to a second catheter branch.

FIG. 11 is a schematic end view of edge protect member shown in FIG. 10.

FIG. 12 is a schematic perspective view of the edge protect member shown in FIG. 10 positioned on a pair of catheter branches.

FIG. 13 is a schematic perspective view of another example edge protect member in accordance with the present disclosure, the edge protect member configured to extend around a circumference of two catheter branches.

FIG. 14 is a schematic end view of edge protect member shown in FIG. 13.

FIG. 15 is a schematic perspective view of the edge protect member shown in FIG. 13 positioned on a pair of catheter branches.

FIG. 22 is a schematic side view of a portion of the stent delivery system shown in FIG. 1 and further includes one of the proximal edge protect members shown in FIGS. 10-21.

FIG. 23 is a schematic perspective view of another example proximal edge protect member configured to receive at least two catheter branches and a portion of an inflatable balloon member.

FIG. 24 is a schematic side view of a portion of the stent delivery system shown in FIG. 1 and further including the proximal edge protect member shown in FIG. 23 with an uninflated main balloon, an unexpanded stent, and a proximal edge protect member.

FIG. 25 is a schematic side view of the stent delivery system shown in FIG. 24, wherein the main balloon is inflated and the stent and proximal edge protect member expanded.

FIG. 26 is a schematic side view of the stent delivery system shown in FIG. 25, wherein the main balloon is deflated, the stent remains expanded, and the proximal edge protect member is elastically recoiled to its original unexpanded state.

FIG. 27 is a schematic cross-sectional view of the stent delivery system shown in FIG. 24 taken along cross-sectional indicators 27-27.

DETAILED DESCRIPTION

General Background

Figure 16:
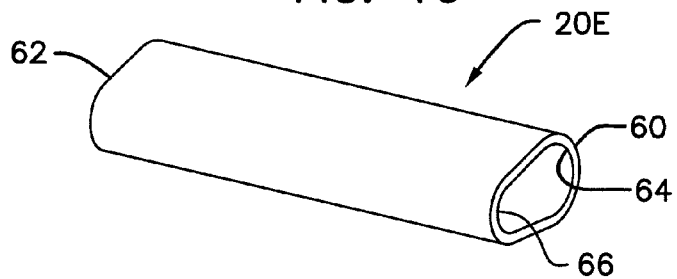
FIG. 16 is a schematic perspective view of another example edge protect member in accordance with the present disclosure, the edge protect member configured to mount to two catheter branches.

This disclosure relates to bifurcation treatment systems, catheter assemblies, and related methods of treating bifurcations in a patient's body. The term bifurcation means a division location from one unit into two or more units. Generally, two types of bifurcations of a body organ include: 1) a main tubular member defining a main lumen and a branch tubular member defining a branch lumen that extends or branches off from the main tubular member, wherein the main and branch lumens are in fluid communication with each other, and 2) a primary or main member defining a primary or main lumen (also referred to as a parent lumen) that splits into first and second branch members defining first and second branch lumens. The term lumen means the cavity or bore of a tubular structure such as a tubular organ (e.g., a blood vessel).

An example bifurcation is a vessel bifurcation that includes a continuous main vessel and a branch vessel, wherein the vessels define a main lumen and a branch lumen, respectively that are in fluid communication with each other. Alternatively, a vessel bifurcation can include a parent vessel that divides into first and second branch vessels, wherein the vessels define a parent lumen and first and second branch lumens, respectively, which lumens are all in fluid communication with each other.

Example applications of the inventive principles disclosed herein include cardiac, coronary, renal, peripheral vascular, gastrointestinal, pulmonary, urinary, and neurovascular systems. The catheter assemblies, systems and methods disclosed herein can be used for locating a branch vessel of the vessel bifurcation and for placement of a stent relative to the vessel bifurcation for treatment of the vessel bifurcation.

While alternatives are possible, the example catheter assemblies disclosed herein include at a distal end portion thereof a main catheter branch and a side catheter branch. The side catheter branch typically includes a side guidewire housing that defines a side guidewire lumen. A distal end portion of the side catheter branch is configured to extend into a branch vessel at a vessel bifurcation. The side catheter branch is used to align features of a stent carried by the proximal end portion of the vessel bifurcation treatment system with an ostium (also referred to as a branch vessel opening) into the branch vessel.

An example main catheter branch can include a catheter shaft having a distal end portion. A main balloon and a side balloon are positioned at the distal end portion of the catheter shaft. A main catheter branch includes a main guidewire housing that defines a main guidewire lumen. The main balloon is positioned along the main guidewire housing. The side balloon is positioned on a side inflation member that extends parallel with the main balloon. The side inflation member defines a side inflation lumen. The side inflation member includes proximal and distal segments that are connected in fluid communication with the side balloon.

One aspect of the present disclosure relates to structures and methods for protecting a proximal end of a stent (sometimes referred to as a proximal edge of the stent) when the stent is being delivered by a catheter assembly to a vessel treatment site (e.g. a vessel bifurcation). In one example arrangement, the main balloon of the main catheter branch of the catheter assembly bulges radially outward at a location just proximal of the proximal end of the stent. This bulging portion of the main balloon extends radially outward at least as far as the proximal end of the stent extends radially outward to provide "protection" of that portion of the distal end of the stent adjacent the main balloon. Although alternatives are possible, the terms protection, protected, and protect in this context generally includes shielding or otherwise guarding that structure (e.g. stent struts) that defines a portion of the distal end of the stent from being engaged by another structure. The other structure in this context can be, for example, a portion of the vessel wall or an open end of a delivery catheter.

Other portions around a circumference of the distal end of the stent might not be "protected" by the bulging portion of the main balloon, such as that portion of the distal end of the stent extending around a portion of the side catheter branch. Providing structure on at least the side catheter branch that extends radially outward a distance at least as great as the stent extends radially outward at the distal end of the stent can provide "protection" of additional portion of the distal end of the stent.

Concerns about protecting a distal end of a stent typically arise when the stent is in an unexpanded state, such as when the stent is crimped onto a catheter assembly, and being positioned at a vessel treatment site (e.g. at a vessel bifurcation) prior to being expanded into engagement with the vessel.

Referring now to FIGS. 1-2, an example catheter assembly 10 is shown and described. The catheter assembly 10 includes a main catheter branch 12, a side catheter branch 14, a stent 16, and a delivery catheter 18. The main catheter branch 12 includes a catheter shaft 30 having a distal end portion 42, a guidewire housing 32, a main balloon 36, a side inflation member 34, and a side balloon 38. The side catheter branch 14 has a distal end portion 70. The stent 16 is operably mounted to the main balloon 36, side inflation member 34, and the side catheter branch 14. The distal end portion 15 of the side catheter branch 14 extends into the stent 16 through a proximal end 82 thereof, and protrudes out of a lateral branch opening 54 at a location along the stent between the distal and proximal open ends 50, 52.

The main and side catheter branches 12, 14 are positioned within the delivery catheter 18 during advancement over main and branch guidewires 26, 28, respectively, to a vessel treatment sight. The guidewire housing 32 of the main catheter branch 12 defines a main guidewire lumen sized to advance over the main guidewire 26. The side catheter branch 14 defines a branch guidewire lumen sized to advance over the branch guidewire 28.

Typically, when the stent delivery system 10 is used to treat a vessel bifurcation, the main catheter branch 12 remains in a main vessel of the vessel bifurcation (not shown) at an axial position that spans an opening into a branch vessel of the vessel bifurcation (not shown). The distal end portion 15 of the side catheter branch 14 extends into a branch vessel of the vessel bifurcation. Positioning the distal end portion 15 in the branch vessel helps to align the lateral branch opening 54 of the stent with an opening into the branch vessel during deployment of the stent 16 at a vessel bifurcation treatment site. The side balloon 30 is configured to extend radially outward relative to the main balloon 28 when the side balloon 30 is inflated. The side balloon 30 is aligned radially and axially with the lateral branch opening 54 of the stent. The side balloon 30, when inflated, typically expands a portion 55 of the stent structure that defines the lateral branch opening 54 of the stent 16 towards the side opening of the branch vessel.

Figure 28:
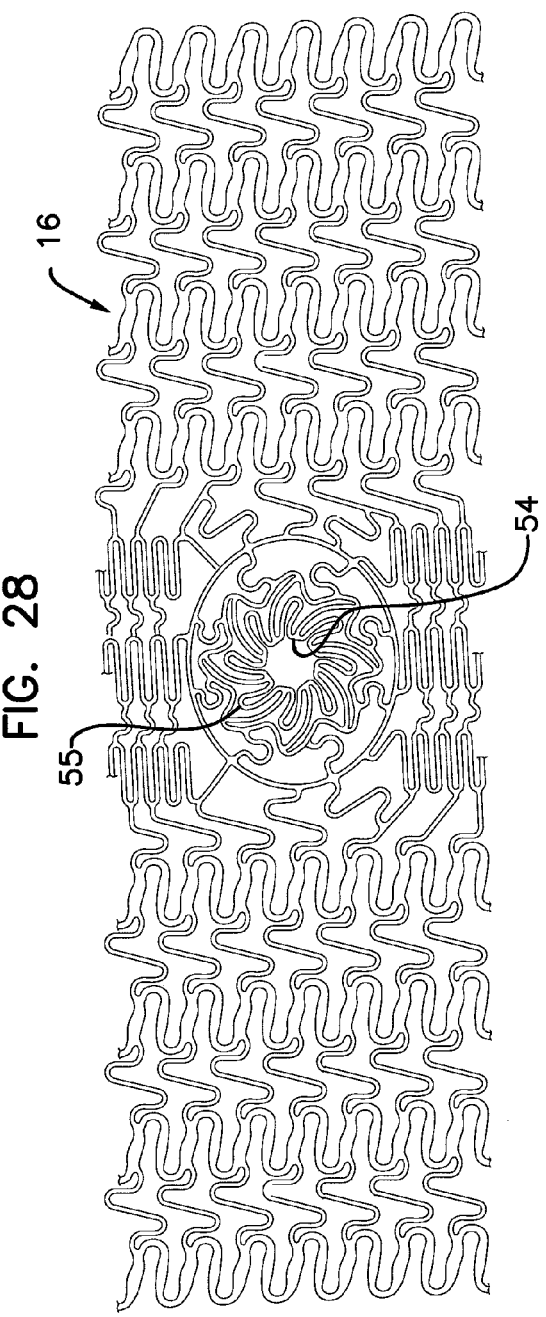
FIG. 28 is a schematic side view of an example stent configuration in accordance with principles of the present disclosure, wherein the stent is in an unexpanded state.
Figure 29:
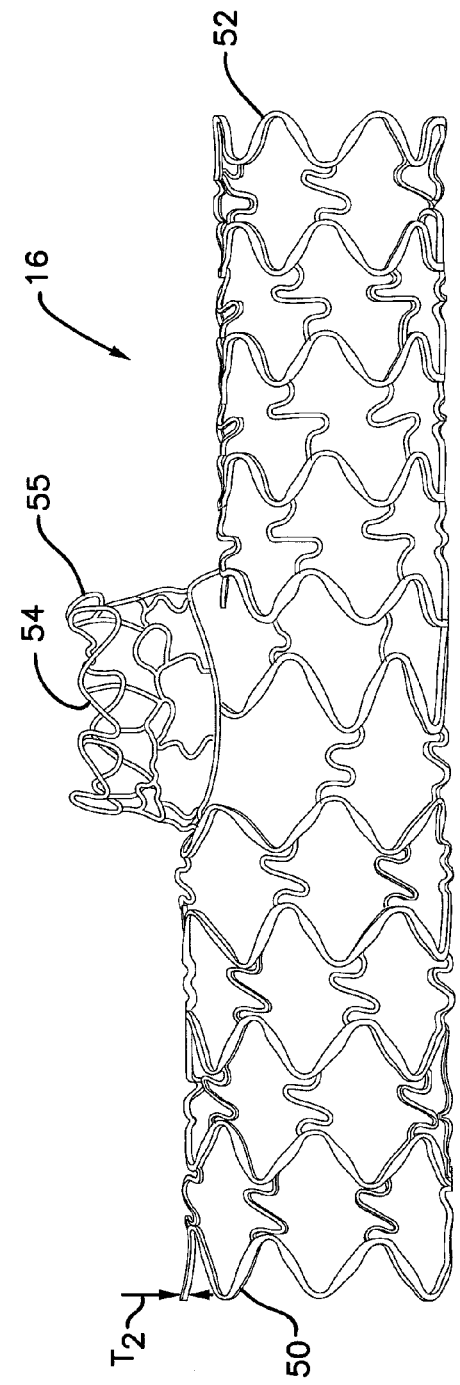
FIG. 29 is a schematic side view of the example stent configuration shown in FIG. 28 with the stent in an expanded state.

FIGS. 1-27 make general reference to a stent 16 in schematic form. FIGS. 28 and 29 provide a more realistic illustration of an example stent that can be used with any of the catheter systems and stent delivery systems described herein. The stent 16 shown in FIGS. 28 and 29 include proximal and distal open ends 50, 52, and a lateral branch opening 54 defined by a plurality of expandable members 55 (sometimes referred to as pedals 55). FIG. 29 shows the expandable members 55 moved into a radial outward extending orientation relative to the generally cylindrical body of the stent 16. Some additional example stent configurations are disclosed in U.S. Published Patent Application No. 2005/0060027, which is incorporated herein by reference in its entirety.

The balloons 36, 38 are illustrated as separate balloons that are positioned adjacent to each other. In other balloon arrangements, the side balloon 38 is positioned on the main balloon 36. For example, the side balloon 38 can be integral with the main balloon 36, or be formed as a separate piece that is secured to the outer surface of the main balloon 36. Alternatively, the side balloon 38 can also be integrated into the side catheter branch 14 or another catheter branch of the catheter assembly, such as described in U.S. Pat. No. 7,220,275, which is incorporated herein by reference.

When using the stent delivery system 10 to treat a vessel bifurcation (not shown), the guidewires 26, 28 are navigated to the treatment site with the main guidewire 26 positioned in the main vessel and the branch guidewire 28 positioned extending from the main vessel into the branch vessel. The stent delivery system 10 is then advanced over the guidewires 26, 28 into a position proximal of the vessel bifurcation within the main vessel. The first and second catheter branches 12, 14 and the stent 16 are removed distally from the delivery catheter 18 either by either advancing distally out of the delivery catheter 18 or by retracting the delivery catheter 18 proximally relative to the branches 12, 14 and the stent 16. The first and second catheter branches 12, 14 and stent 16 are then positioned in alignment with the vessel bifurcation. In some circumstances, the stent 16 must be drawn proximally back into the delivery catheter 18 in order to obtain improved orientation relative to the vessel bifurcation. One common reason for retracting the stent 16 back into the delivery catheter 18 is the occurrence of relative twist between the guidewires 26, 28 in the area of the vessel bifurcation. The use of multiple guidewires in treatment of vessel bifurcations can lead to increased instances of retracting the stent 16 back into the delivery catheter 18.

Retracting the stent 16 back into the delivery catheter 18 can result in damage to the stent 16. The proximal end portion 50 of stent 16 is typically positioned radially outward from portions of the main and side catheter branches 12, 14 positioned just proximal of the stent 16. The proximal end portion 50 of stent 16 can be susceptible to catching on the distal end 19 of the delivery catheter 18 as the stent 16 (while mounted on the main and side catheter branches 12, 14) is retracted back into the delivery catheter 18.

When the stent proximal end portion 50 catches on the end of the delivery catheter 18, struts that define the end portion of stent 16 can be unintentionally bent or deformed. Bent and deformed struts can pose potential problems such as, for example, not expanding properly when the main balloon inflates, not advancing and aligning properly at the vessel bifurcation, or causing damage to the vessel wall.

One partial solution to this problem has been to purposely provide excess amounts of the main balloon 36 positioned proximal of the stent 16. This excess portion of the main balloon 36 is sometimes referred to as a "balloon cone", a "balloon cone puff", or a "balloon bulge portion" 44. The balloon cone puff 44 extends radially outward to the same or a further radial position as the radial position of the proximal end portion of the stent 16 relative to the guidewire member 32. The balloon cone puff can provide a transition surface from an outer surface of the catheter shaft to the outer surface of the stent 16 wherein the proximal end portion 50 of the stent 16 is protected from engagement.

In the stent delivery system 10, which includes multiple catheter members (i.e., catheter shaft 30, side inflation member 34, and side catheter branch 14) extending into the proximal end of stent 16, the balloon cone puff 44 of the main balloon 36 might not provide adequate protection of the entire circumference of the proximal end portion 50 of the stent 16. That portion of the proximal end portion 50 of stent 16 surrounding the side catheter branch 14 and side inflation member 34 can be left unprotected even when balloon cone puff 44 is present (see FIGS. 1 and 2). Although alternatives are possible, the examples described in further detail below provide for edge protection of additional portions around the circumference of the stent proximal end portion 50 using various stent edge protect arrangements in place of or in addition to the balloon cone puff 44.

The Example Stent Edge Protect Members of FIGS. 3-9

Referring now to FIGS. 3-6, an example edge protect member 20 is shown and described. The edge protect member 20 generally includes distal and proximal ends 60, 62, a constant inner dimension $D_1$, and an outer maximum dimension $D_2$ measured at the distal end 60. The outer maximum dimension of the edge protect member 20 defined by an outer surface thereof can vary along the length of the edge protect member. FIG. 4 illustrates how the thickness $T_1$ and related outer dimension $D_2$ of the edge protect member 20 diminishes when moving from the distal end 60 to the proximal end 62. This tapered construction provides for a relatively smooth transition from an outer surface of the catheter branch at the proximal end of the edge protect member 20 to the outer surface of a stent at the proximal end of the stent adjacent to the distal end 60 of the edge protect member 20 (see FIG. 6).

FIG. 5 illustrates the edge protect member 20 mounted to the side catheter branch 14. FIG. 6 illustrates the side catheter branch 14 having the edge protect member 20 positioned thereon at a location just proximal of the proximal end 50 of the stent 16. The tapered construction of the edge protect member 20 provides for the relatively smooth transition surface described above, which can promote protection of the proximal end portion of the stent 16 during retraction of the stent 16 back into a delivery catheter 18 (see FIG. 1). Preferably, a wall thickness $T_1$ (see FIG. 4) of the edge protect member 20 at the distal end 60 is sufficiently thick so that an outer surface of the edge protect member 20 at the distal end 60 protrudes radially outward at least as far as the outer surface of the distal end 60 of the edge protect member 20. In some cases, it is desirous to have the edge protect member 20 extend further radially outward than the maximum radial outward position of the stent 16 at the stent proximal end portion 50.

Although alternatives are possible, the thickness $T_1$ is generally at least as great as a thickness $T_2$ (see FIG. 29) of the stent 16 at the proximal open end 52. Alternatively, the thickness $T_1$ can be less than the thickness $T_2$. In one arrangement, the thickness $T_1$ is in the range of about 50% to about 300% of the thickness $T_2$, inclusive, and more preferably in the range of about 50% to about 150% of the thickness $T_2$.

In some arrangements, the edge protect member 20 can have a uniform wall thickness between the distal and proximal ends 60, 62. As a result, retraction of the main catheter branch 12, side catheter branch 14, and stent 16 back into the delivery catheter 18 results in engagement with the proximal end of the edge protect member 20 rather than some portion of the stent 16. Damage to a portion of the edge protect member 20 can be relatively insignificant as compared to potential damage to the stent 16.

In some arrangements, the edge protect member 20 defines a tapered wall thickness construction as part of the process of heat bonding the edge protect member 20 to the side catheter branch 14. A hot jaw or other device (not shown) used for applying the heat can impose a finished shape upon the edge protect member 20 while it is in a molten state that results in a desired tapered construction that provides a relatively smooth transition between the outer surface of the side catheter branch 14 and the outer surface of the stent 16 at the proximal end 60.

The cross-sectional shape and size of the edge protect member 20 can vary in different arrangements. Although many alternatives exist, some of which are described below, FIGS. 7 and 8 illustrate two alternative cross-sectional shapes for edge protect member 20A, 20B, respectively. Edge protect member 20A generally includes a cross-sectional shape with increased width portions 72 and a reduced thickness 70 along a bottom side of the edge protect member 20A that is opposite an increased thickness portion 76. The increased thickness portion 76 is preferably positioned adjacent to the stent proximal end portion 50. The reduced thickness portion 74 can provide a reduced overall profile for the stent delivery system 10. The reduced thickness portion 74 generally provides closer positioning of the edge protect member 20A adjacent to either or both of the other branches or inflation members of the stent delivery system at a location proximal of the stent 16.

FIG. 8 illustrates another edge protect member 20B that has an increased thickness portion 76 that extends around the periphery of the edge protect member 20A except at a limited periphery region (e.g., across the bottom side 70 thereof) that has a reduced thickness 74. The bottom portion 70 of the edge protect member 20B in the area of a reduced thickness portion 74 can be contoured or otherwise shaped in any way desired to more closely match an outer profile of the other catheter branch of inflation member positioned that is engaged by the reduced thickness portion 74.

FIG. 9 illustrates a portion of a stent delivery system that includes one of the edge protect members 20A, 20B. FIG. 9 illustrates how the increased thickness portion 76 provides edge protection of the proximal end portion 50 of the stent 16 while a bottom side of the edge protect member 20 remains generally constant so as to minimize the overall profile of the stent delivery system 10.

The edge protect members 20-20B can be secured to the catheter branch 14 at the same time as the addition of a marker band sleeve 24 (see FIG. 5). Typically, a marker band sleeve is used to enclose one or more marker bands 22 that are positioned on the catheter branch 14 at a location distal of the edge protect member 20-20B. One or more marker bands 22 can be positioned under the stent 16 (see FIG. 6). In some cases, the marker band sleeve 24 can be secured in place using the same connection means (e.g., adhesive or heat bonding) that is used to secure the edge protect member 20-20B in place. Securing both the edge protect member and the marker band sleeve in place at the same time can eliminate a manufacturing step for the system 10.

The Example Stent Edge Protect Members of FIGS. 10-22

FIGS. 10-22 illustrate several additional edge protect member configurations 20C-F. The edge protect members 20C-F are configured to be positioned on or otherwise mounted to two separate tubular members (e.g., main catheter branch 12, side catheter branch 14, and side inflation member 34). As described above, edge protection of the stent proximal end portion in the area surrounding the main catheter branch 12 is provided by the balloon cone puff 44 of the main balloon 36. The edge protect members 20C-F are configured for use with the side catheter branch 14 and side inflation member 34, alone or in combination with a balloon cone puff 44.

The edge protect member 20C shown in FIGS. 10-12 generally includes a first branch recessed portion 64 that includes an unbroken circumference structure, and a second branch recessed portion 66 that is broken around its circumference. A connecting portion 68 spans between the first and second branch recessed portions 64, 66 to provide a unitary single piece construction for the edge protect member 20C. A tapered portion 78 can be included at the proximal end 62 of each of the first and second branch recessed portions 64, 66 (see FIG. 10).

The enclosed first branch recessed portion 64 is sized in this configuration for receiving the side catheter branch 14. Typically, the side catheter branch 14 is inserted into the first branch recessed portion 64 and positioned at a desired axial location relative to the edge protect member 20C. The side inflation member 34 is either inserted into the proximal or distal open end of the second branch recess portion 66, or the second branch recess portion 66 is opened radially an amount sufficient to clip or otherwise fit around the outer surface of the side inflation member 34.

After the edge protect member 20C is positioned properly relative to each of the side catheter branch 14 and side inflation member 34, the edge protect member 20C is secured to at least one of the members 14, 34 using, for example, adhesives or heat bonding. The use of adhesives may have some advantages in certain circumstances, while heat bonding has advantages in other circumstances. One advantage of using heat bonding is the ability to reshape and form portions of the edge protect member 20C after positioning on the members 14, 34. Heat bonding also can result in a unitary construction of the edge protect member 20C with the side catheter branch 14 and side inflation member 30 due to reflow of the edge protect member material.

The second branch recess portion 66 is shown having a shorter length than the first branch recessed portion 64. One reason for this stepped construction is that the length of the side inflation member 34 proximal of the stent 16 can be relatively short in some constructions of the stent delivery system 10. For example, a dual bond construction is possible in which the side inflation member 34, main balloon 36, and catheter shaft 30 are secured together at a single bond location relatively close (e.g., within about 10 mm) to the proximal end of the stent 16. In such a construction, the second branch recess portion 66 must be shortened in order to fit between the proximal end of the stent 16 and the dual bond location. In other constructions wherein the bond between the proximal end of the side inflation member 34 and the catheter shaft 30 is spaced proximal of the main balloon 36, additional length can be made available along the side inflation member 34 for attachment of the second branch recess portions 66.

Referring now to FIGS. 13-15, another example edge protect member 20D is shown and described. The edge protect member 20D includes first and second branch recessed portions 64, 66 that are each individually enclosed to define two separate lumens. The first branch recessed portion 64 is sized to receive the side catheter branch 14, and the second branch recess portion 66 is sized to receive the side inflation member 34. An advantage of the construction of edge protect member 20D is that there are ample amounts of material available at every location around the circumference of the members 14, 34 for reflow and positive connection with the edge protect member 20D. Another advantage of the construction of edge protect member 20 is the amount of edge protection actually provided. The outer circumference and shape of the edge protect member 20 at its distal end 60 can be constructed in any desired way to provide maximum edge protection of the proximal stent end portion. The D-shaped construction of the edge protect member 20 can also provide certain advantages related to enhanced edge protection while minimizing the overall thickness of the stent delivery system 10. The D-shaped construction can also provide for improved ease in manufacturing, such as improved ease in handling and assembly of parts.

Figure 17:
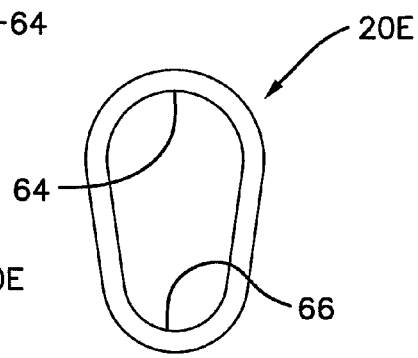
FIG. 17 is a schematic end view of edge protect member shown in FIG. 16.
Figure 18:
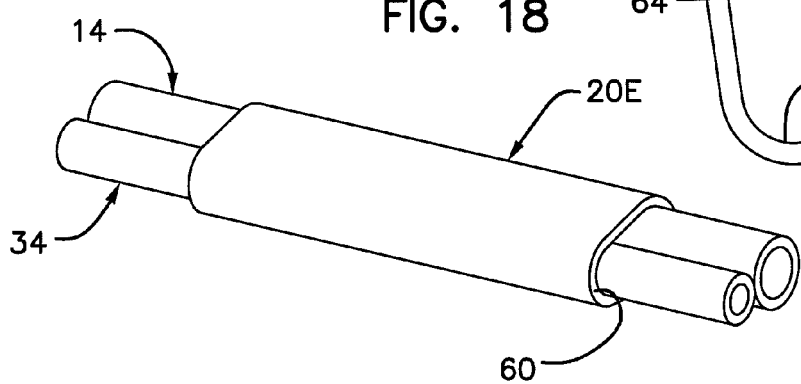
FIG. 18 is a schematic perspective view of the edge protect member shown in FIG. 16 positioned on a pair of catheter branches.

FIGS. 16-18 illustrate another edge protective member 20E wherein the first and second branch recessed portions 64, 66 are open to each other and defined as a single lumen. Each of the side catheter branch 14 and side inflation member 34 is inserted into the edge protect member 20E. The shape of the edge protect member 20E can improve manufacturability compared to other example edge protect members described herein. The edge protect member 20E can provide a relatively efficient arrangement for proper axial positioning of the edge protect member 20 relative to each of the side catheter branch 14 and side inflation member 34. The elimination of material of the edge protect member 20E between the side catheter branch 14 and side inflation member 34 can provide for further reduction in overall outer profile of the stent delivery system 10.

Figure 19:
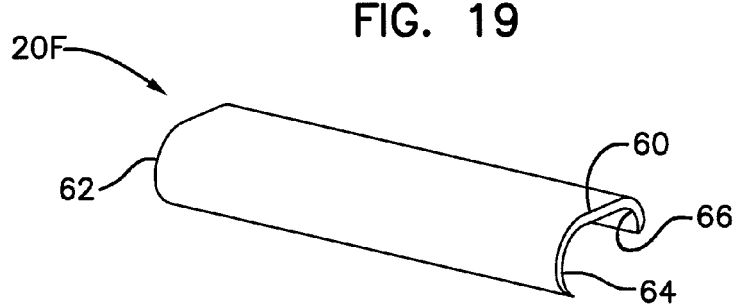
FIG. 19 is a schematic perspective view of another example edge protect member in accordance with the present disclosure, the edge protect member configured to mount to two catheter branches without extending around the circumference of either of the catheter branches.
Figure 20:
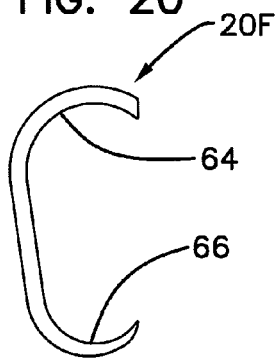
FIG. 20 is a schematic end view of edge protect member shown in FIG. 19.
Figure 21:
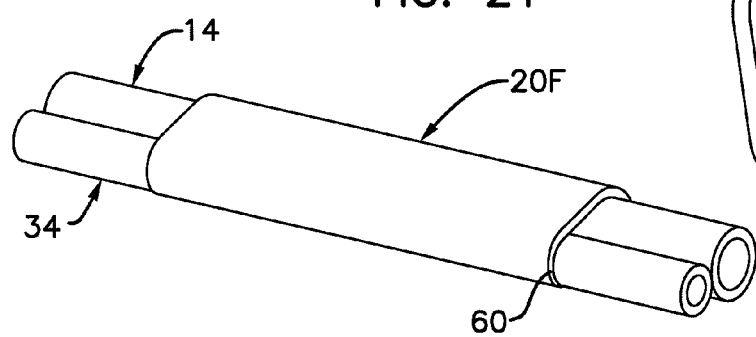
FIG. 21 is a schematic perspective view of the edge protect member shown in FIG. 19 positioned on a pair of catheter branches.

FIGS. 19-21 illustrate a still further edge protect member 20F. The edge protect member 20F, like edge protect member 20E, defines first and second branch recessed portions 64, 66 that are open to each other. Edge protect member 20F further has eliminated one of the entire side walls thereof. This eliminated material from the edge protect member 20F can reduce the overall profile of the stent delivery system 10. In one arrangement, the edge protect member 20F can be constructed to snap-fit over the side catheter branch 14 and side inflation member 34. In other arrangements, the edge protect member 20F is constructed such that at least one of the side catheter branch 14 and side inflation member 34 is inserted into at least one of the recessed portions 64, 66 at one of the distal and proximal ends 60, 62.

FIG. 22 illustrates a dual lumen edge protect member (i.e., one of the edge protect members 20C-F) positioned on the side catheter branch 14 and side inflation member 34 of the stent delivery system 10. FIG. 22 illustrates how the edge protect member 20C-F provides edge protection for a large portion of the proximal end portion 50 of the stent 16 for those portions of the edge 50 not already protected by the balloon cone puff 44 of the main balloon 36. The edge protect members 20C-F provide at least edge protection of those proximal struts on the stent that come in contact with the side catheter branch 14 and side inflation lumen 34, and preferably at least some of those proximal struts positioned between the side catheter branch 14 and side inflation member 34.

A further advantage of securing the side catheter branch 14 and side inflation member 34 together beyond the edge protection functions described above is the assistance in aligning the side balloon 38 relative to the lateral branch opening 54 during crimping of the stent 16 as part of the process of assembling the stent delivery system 10. This alignment of the side balloon 38 relative to the lateral branch opening 54 is a significant consideration for consistent deployment of the stent 16. With the numerous individual parts involved in the stent delivery system 10, which must be all properly aligned and held stable while crimping the stent, to provide connection of at least two of those parts (i.e., the side catheter branch 14 and side inflation member 34) can improve the repeatability of ensuring alignment of the side balloon 38 with the lateral branch opening 54 during assembly.

Many other shapes, sizes, material thicknesses, and combinations of features described with reference to FIGS. 10-22 are possible for each of the edge protect members 20C-F.

The Example Stent Edge Protect Members of FIGS. 23-27

Referring now to FIGS. 23-27, another example edge protect member 20G is shown and described. The edge protect member 20G defines a single recessed portion 64 (also referred to as a cavity, lumen, or internal space) that is sized to receive all of the components of the stent delivery system 10 that are proximal of the stent 16 with exception of the delivery catheter 18.

FIG. 24 illustrates the edge protect member 20G positioned just proximal of the proximal end 50 of the stent 16. The edge protect member 20G is constructed to provide proximal edge protection of the stent 16 around an entire circumference of the proximal end 50 of the stent 16. The edge protect member 20G provides proximal edge protection of the stent 16 around an entire circumference as shown in FIG. 27. Typically, the outer surface of the edge protect member 20G at its proximal end 60 at every location around its periphery is oriented at the same radial position or a greater radial position as compared to an outer periphery surface of the stent 16 at the proximal end 50 to provide maximum proximal edge coverage.

One consideration involved in enclosing a portion of the main balloon 36 within the edge protect member 20G is that the edge protect member 20G can be capable of expanding and contracting as the main balloon 36 expands and contracts. FIGS. 25 and 26 illustrate how the edge protect member 20G expands and then contracts with the main balloon 36 during expansion of the stent 16. Some example elastic materials that can be used in the edge protect member 20G that provide this expansion and contraction include, for example, silicone or polyurethanes such as pellathane and techothane. Although alternatives are possible, the edge protect member 20G generally can expand with no significant resistance during deployment of the stent 16 and then return to its original shape so as not to add significant resistance during withdrawal of the stent delivery system 10 after the stent 16 has been expanded into engagement with the vessel wall.

One advantage of the edge protect member 20 is that it can be positioned and secured in place after the stent has been crimped to the main and side catheter branches 12, 14 and side inflation member 34 with the side balloon 38 in proper radial and axial alignment with the lateral branch opening 54. The ability to add the edge protect member in a later assembly step can be advantageous because the edge protection can be provided without having to increase the number of assembly parts needed to be aligned at the crimping step. Providing elastic properties in edge protect member 20G can also be advantageous in that the internal recessed portion 64 can be enlarged during assembly to be relatively easy to position in place slid over the main and side catheter branches 12, 14 and side inflation member 34, and then retracted to minimize the overall outer profile of the system 10. The elastic properties of the edge protect member 20G can also help reduce the profile of the balloon cone puff 44 if the balloon cone puff 44 extends too far radially outward beyond the stent 16. The elastic properties of the edge protect member 20G are applicable to many other catheter arrangements besides the vessel bifurcation treatment system shown with reference to the drawings included herein.

The edge protect member 20G can be secured in a given axial or radial position by attachment to at least one of the main catheter branch 12, side catheter branch 14, and side inflation member 34. Securing can be done using, for example, an adhesive or heat bonding to one or more of the features of the stent delivery system 10 that are positioned proximal of the stent 16.

Materials and Other Considerations

The size and shape of the various edge protect members described with reference to FIGS. 1-27 can vary depending on the particular application. In one example, the edge protect member has a total length no greater than about 20 mm, preferably about 3 to about 15 mm, and more preferably about 5 to about 10 mm. The maximum internal dimension of each of the recess portions (e.g., first and second branch recessed portions 64, 66) is typically about 0.5 to about 1 mm, preferably about 0.55 to about 0.75 mm, and more preferably about 0.58 to about 0.71 mm. The thickness of the side wall of any given portion of the edge protect member is preferably no less than about 0.05 mm, or more preferably about 0.05 to about 0.2 mm, and most preferably about 0.1 to about 0.13 mm in thickness.

The edge protect members 20-20G described above can be formed using various methods and processes. In one example, the edge protect member is formed as an elongate extruded member that is cut to a desired length. Some types of extruding techniques can provide non-circular cross-sectional shapes and tapered exterior surfaces that are desired for the edge protect member. In another example, the edge protect member is molded as a single piece using, for example, an injection or blow molding process. Molding techniques can produce complex features, even in the small scale required for the edge protect members described herein.

The example systems disclosed herein may be used in over-the-wire or rapid exchange systems. Some example rapid exchanges systems are disclosed in U.S. Published Patent Application No. 2003/0181923 to Vardi et al., which application is incorporated herein by reference.

The materials used in the balloons, catheter shafts, and edge protect members disclosed herein can be made of any suitable material including, for example, thermoplastic polymers, polyethylene (high density, low density, intermediate density, linear low density), various copolymers and blends of polyethylene, ionomers, polyesters, polycarbonates, polyamides, poly-vinyl chloride, acrylonitrile-butadiene-styrene copolymers, polyether-polyester copolymers, and polyether-polyamide copolymers. One suitable material is Surlyn®, a copolymer polyolefin material (DuPont de Nemours, Wilmington, Del.). Still further suitable materials include thermoplastic polymers and thermoset polymeric materials, poly (ethylene terephthalate) (commonly referred to as PET), thermoplastic polyamide, polyphenylene sulfides, polypropylene. Some other example materials include polyurethanes and block copolymers, such as polyamide-polyether block copolymers or amide-tetramethylene glycol copolymers. Additional examples include the PEBAX® (a polyamide/polyether/polyester block copolymer) family of polymers, e.g., PEBAX® 70D, 72D, 2533, 5533, 6333, 7033, or 7233 (available from Elf AtoChem, Philadelphia, Pa.). Other examples include nylons, such as aliphatic nylons, for example, Vestamid L21011F, Nylon 11 (Elf Atochem), Nylon 6 (Allied Signal), Nylon 6/10 (BASF), Nylon 6/12 (Ashley Polymers), or Nylon 12. Additional examples of nylons include aromatic nylons, such as Grivory (EMS) and Nylon MXD-6. Other nylons and/or combinations of nylons can also be used. Still further examples include polybutylene terephthalate (PBT), such as CELANEX® (available from Ticona, Summit, N.J.), polyester/ether block copolymers such as ARNITEL® (available from DSM, Erionspilla, Ind.), e.g., ARNITEL® EM740, aromatic amides such as Trogamid (PA6-3-T, Degussa), and thermoplastic elastomers such as HYTREL® (Dupont de Nemours, Wilmington, Del.). In some embodiments, the PEBAX®, HYTREL®, and ARNITEL® materials have a Shore D hardness of about 45 D to about 82 D. The balloon materials can be used pure or as blends. For example, a blend may include a PBT and one or more PBT thermoplastic elastomers, such as RITEFLEX® (available from Ticona), ARNITEL®, or HYTREL®, or polyethylene terephthalate (PET) and a thermoplastic elastomer, such as a PBT thermoplastic elastomer. Additional examples of balloon material can be found in U.S. Pat. No. 6,146,356. It should be understood that the specific materials disclosed below for the individual embodiments does not limit the embodiment to those materials.

In the example catheter assemblies described above, some of the features can include a lubricious coating on an exterior surface thereof. The coating can promote insertion of the branch balloon into the branch vessel of a vessel bifurcation. The coating can also improve removal of the branch balloon from the branch vessel and the branch aperture of the stent when deflating and removing the catheter assembly from the vessel bifurcation after expansion of the stent. Some example coatings for use with the branch balloon include hydrophilic polymers such as polyarylene oxides, polyvinylpyrolidones, polyvinylalcohols, hydroxyl alkyl cellulosics, algins, saccharides, caprolactones, and the like, and mixtures and combinations thereof. Hydrophilic polymers can be blended among themselves or with formulated amounts of water insoluble compounds (including some polymers) to yield coating with suitable lubricity, bonding and solubility. In some examples, portions of the devices described herein can be coated with a hydrophilic polymer or a fluoropolymer such as polytetrafluoroethylene (PTFE), better known as TEFLON®.

While the example stent delivery systems described above illustrate a balloon expandable stent having a predetermined side opening (i.e., branch aperture), other types of stents can be used with the catheter features described above. A variety of stents can be used with the systems and methods disclosed herein. Examples of such stents can be found in, for example, in U.S. Pat. Nos. 6,210,429, 6,325,826 and 7,220,275 the entire contents of which are incorporated herein by reference. In general, the aforementioned stents have a tubular shape with a continuous sidewall that extends between the proximal and distal ends. Proximal and distal stent apertures are defined at respective proximal and distal ends of the stent. A branch aperture is defined in the sidewall of the stent. The branch aperture provides access between an interior of the stent and an exterior of the stent. In some stents, the branch aperture includes expandable structure around a peripheral edge thereof that expands in a generally radial outward direction relative to a longitudinal axis of the stent. The expandable structure can be configured to extend into the branch lumen of the bifurcation upon expansion of the stent. The stent includes a plurality of strut structures that define the sidewall. The struts are expandable from a first, unexpanded state to a second, expanded state. Typically, the stent is configured to maintain the expanded state. The struts define a plurality of cell openings or cells along a length of the stent. The size and shape of the cells is typically different than the size and shape of the branch aperture. The stent is typically expanded once the stent is properly positioned in the main lumen of the bifurcation with the branch aperture aligned radially and axially with an opening into the branch lumen. The stent, including the expandable structure surrounding the branch aperture, can be expanded with a single expansion or with multiple expansions using, for example, one or more inflatable balloons.

CONCLUSION

One aspect of the present disclosure relates to a catheter assembly that includes a stent, a first catheter branch, a second catheter branch, and a stent edge protect member. The stent includes a plurality of expandable struts that define a distal open end, a proximal open end, a side branch aperture, an exterior surface, and an interior volume of the stent. The first catheter branch includes at least a main balloon member and extends through the interior volume of the stent from the proximal open end to the distal open end. The second catheter branch extends through the interior volume of the stent from the proximal open end and out through the side branch aperture. The stent edge protect member is separate from the main balloon and includes a distal end portion positioned proximal of the stent proximal open end at a location adjacent to the proximal open end of the stent. The stent edge protect member is positioned on at least one of the first and second catheter branches. At least the distal end portion of the stent edge protect member has a thickness measured in a radial direction that is at least as great as a thickness of the stent struts at the distal open end measured in the radial direction.

Another aspect of the present disclosure relates to a catheter assembly that includes a stent, a first catheter branch, a second catheter branch, and a stent. The stent includes a distal open end, a proximal open end, and an exterior surface. The first catheter branch includes a first balloon member and extends the stent from the proximal open end to the distal open end with at least a portion of the balloon member positioned within the stent. The second catheter branch extends through at least a portion of the stent. The stent edge protect member is arranged as a separate piece from the first catheter branch and includes a distal end portion. The stent edge protect member is arranged with the distal end portion positioned proximal of and adjacent to the proximal open end of the stent. At least the distal end portion of the stent edge protect member extends radially outward relative to the first catheter branch to a position a distance at least as great as a radial outward position of the exterior surface of the stent relative at the distal open end.

A still further aspect of the present disclosure relates to a method of treating a vessel with a stent delivery system. The stent delivery system includes a catheter assembly and a delivery catheter. The catheter assembly includes a stent, a first catheter branch, a second catheter branch, and a stent edge protect member. The first catheter branch includes a first balloon member. The stent includes a proximal open end and a distal open end, wherein the first and second catheter branches extend into the proximal open end of the stent. The delivery catheter defines a distal open end and a lumen sized to receive the catheter assembly. The stent edge protect member is provided as a separate piece from the first catheter branch and is positioned with a distal end portion of thereof arranged proximal of and adjacent to the proximal open end of the stent. The stent edge protect member has a thickness at the distal end portion that is at least as great as a thickness of the stent at the proximal open end. The method includes advancing the stent delivery system distally to a treatment site, and advancing the catheter assembly distally out from the distal open end of the delivery catheter, wherein a proximal end of the stent is spaced distal of the distal open end of the delivery catheter. The method can also include after advancing the catheter assembly, retracting a portion of the catheter assembly proximally back into the delivery catheter, wherein the proximal open end of the stent is positioned proximal of the distal open end of the delivery catheter. The stent edge protect member can limit engagement of the proximal open end of the stent on the distal open end of the delivery catheter during retracting of the catheter assembly.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A catheter assembly, comprising:
    (a) a stent, the stent having a plurality of expandable struts that define a distal open end, a proximal open end, a side branch aperture, an exterior surface, and an interior volume of the stent, the stent having a compressed configuration and an expanded configuration;
    (b) a first catheter branch, the first catheter branch including a catheter shaft defining a main guidewire housing, at least a main balloon member positioned on the catheter shaft, a side inflation member, a side balloon member positioned on the side inflation member, the first catheter branch extending through the interior volume of the stent from the proximal open end to the distal open end;
    (c) a second catheter branch, the second catheter branch extending through the interior volume of the stent from the proximal open end and out through the side branch aperture; and
    (d) a stent edge protect member separate from the main balloon, the stent edge protect member having a distal end portion positioned proximal of the stent proximal open end at a location adjacent to the proximal open end of the stent in both the compressed and expanded configurations, at least the distal end portion of the stent edge protect member having a thickness measured in a radial direction that is at least as great as a thickness of the stent struts at the distal open end measured in the radial direction, wherein the stent edge protect member is fixed in a predetermined axial or radial position on only the side inflation member and the second catheter branch, wherein the stent edge protect member tapers from a first outer diameter at a distal end to a second outer diameter at a proximal end, wherein the first outer diameter is larger than the second outer diameter, wherein the taper provides a transition surface between the exterior surface of the stent and an outer surface of at least one of the first and second catheter branches, wherein the stent edge protect member has a constant inner dimension from the distal end to the proximal end.

2. The catheter assembly of claim 1, wherein the stent edge protect member includes a first portion sized to receive at least a portion of the side inflation member and a second portion sized to receive at least a portion of the second catheter branch.

3. The catheter assembly of claim 2, wherein the first portion has a first length and the second portion has a second length, the first length being greater than the second length.

4. The catheter assembly of claim 1, wherein the stent edge protect member defines a first lumen sized to receive at least a portion of the side inflation member and a second lumen sized to receive at least a portion of the second catheter branch.

5. The catheter assembly of claim 1, wherein the stent edge protect member defines a single lumen sized to receive at least a portion of the side inflation lumen and at least a portion of the second catheter branch.

6. The catheter assembly of claim 1, wherein the stent edge protect member includes a c-shaped cross-section.

7. The catheter assembly of claim 1, wherein the stent edge protect member is positioned on the second catheter branch and not on the first catheter branch.

8. The catheter assembly of claim 1, wherein a thickness of the stent edge protect member decreases when moving from the distal end to the proximal end.

9. A catheter assembly, comprising:
   (a) a stent, the stent having a distal open end, a proximal open end, and an exterior surface, the stent having a compressed configuration and an expanded configuration;
   (b) a first catheter branch, the first catheter branch including a first balloon member, the first catheter branch extending through the stent from the proximal open end to the distal open end with at least a portion of the balloon member positioned within the stent;
   (c) a second catheter branch extending through at least a portion of the stent; and
   (d) a stent edge protect member, the stent edge protect member being a separate piece from the first catheter branch and including a distal end portion, the stent edge protect member being arranged with the distal end portion positioned proximal of and adjacent to the proximal open end of the stent in both the compressed and expanded stent configuration, at least the distal end portion of the stent edge protect member extending radially outward relative to the first catheter branch to a position at least a distance as great as a radial outward position of the exterior surface of the stent in the expanded configuration, relative to the first catheter branch at the distal open end, and the stent edge protect member defining only a single lumen sized to receive at least a portion of the first catheter branch and at least a portion of the second catheter branch, wherein the stent edge protect member is fixed in a predetermined axial or radial position directly to at least one of the first and second catheter branches, such that the stent edge protect member remains in place when the stent is expanded, wherein the stent edge protect member has a constant inner dimension from a distal end to a proximal end.

10. The catheter assembly of claim 9, wherein the stent edge protect member defines a single lumen sized to receive the catheter shaft, the side inflation member, and the second catheter branch.

11. The catheter assembly of claim 9, wherein the stent edge protect member expands and contracts upon inflation and deflation of the main balloon member.

12. The catheter assembly of claim 9, wherein the stent edge protect member comprises an elastic material.

13. The catheter assembly of claim 9, wherein the stent edge protect member has an outer diameter that is at least as great as an outer diameter of the exterior surface of the proximal open end of the stent along an entire circumference of the proximal open end of the stent.

14. A catheter assembly, comprising:
   a stent, the stent having a plurality of expandable struts that define a distal open end, a proximal open end, a side branch aperture, an exterior surface, and an interior volume of the stent, the stent having a compressed configuration and an expanded configuration;
   a first catheter branch, the first catheter branch including at least a main balloon member and a side inflation member, the first catheter branch extending through the interior volume of the stent from the proximal open end to the distal open end;
   a second catheter branch, the second catheter branch extending through the interior volume of the stent from the proximal open end and out through the side branch aperture; and
   a stent edge protect member separate from the main balloon and the side balloon, the stent edge protect member having a distal end portion positioned proximal of the stent proximal open end at a location adjacent to the proximal open end of the stent in both the compressed and expanded stent configurations, the stent edge protect member having an inner diameter configured to surround both the first catheter branch and the second catheter branch, wherein the inner diameter is constant from a distal end to a proximal end of the stent edge protect member, wherein the stent edge protect member is fixed in a predetermined axial or radial position directly on at least one of the first and second catheter branches, wherein the stent edge protect member expands and contracts upon inflation and deflation of the main balloon member, wherein an outer surface of the stent edge protect member at every location around a periphery is oriented at the same or a greater radial position compared to an outer periphery surface of the proximal open end of the stent.

15. The catheter assembly of claim 14, wherein the first catheter branch further includes a catheter shaft, a side balloon member positioned on the side inflation member, and a main guidewire housing extending through the main balloon member, the stent edge protect member positioned on at least one of the catheter shaft, the side inflation member, and the second catheter branch.

* * * * *